United States Patent
Verma et al.

(10) Patent No.: US 6,326,138 B1
(45) Date of Patent: Dec. 4, 2001

(54) FUNCTIONAL ASSAYS FOR THE IDENTIFICATION OF LIGANDS WHICH MODULATE SIGNAL TRANSDUCTION

(75) Inventors: Inder M. Verma, Solana Beach; Keith A. Cauley, San Diego, both of CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 08/342,242

(22) Filed: Nov. 18, 1994

Related U.S. Application Data

(63) Continuation of application No. 08/001,115, filed on Jan. 5, 1993, now abandoned.

(51) Int. Cl.[7] .............................. C12Q 1/68; G01N 33/53
(52) U.S. Cl. .............................. 435/6; 435/7.21; 435/7.4; 435/7.9
(58) Field of Search .................. 435/6, 7.21, 7.4, 435/7.9, 96.8; 436/518, 540, 546, 548

(56) References Cited

U.S. PATENT DOCUMENTS

| | | | |
|---|---|---|---|
| 5,015,571 | * 5/1991 | Niman et al. | 435/7.92 |
| 5,342,942 | * 8/1994 | Jaen et al. | 544/250 |
| 5,418,135 | * 5/1995 | Pang et al. | 435/7.1 |

OTHER PUBLICATIONS

Kelley et al., Cell–Specific Regulation of the c–myc Gene by Lymphocyte Mitogens and Platelet–Derived Growth Factor, Cell, vol. 35, pp. 603–610 (1983).*
Lamph et al., Induction of proto–oNcogene JUN/AP–1 by serum and TPA, Nature, vol. 334, pp. 629–631 (1988).*
Bartlett and Banker, "An Electron Microscopic Study of the Development of Axons and Dendrites by Hippocampal Neurons in Culture," *Neuroscience*4: 1944–1953 (1984).
Curran et al., "Viral and Cellular *fos* Proteins: A Comparative Analysis," *Cell*36:259–268 (1984).
Curran et al., "Viral and Cellular *fos* Proteins Are Complexed with a 39,000–Dalton Cellular Protein," *Molecular and Cellular Biology*5: 2251–2256 (1985).
De Togni et al., "Detection of *fos* Protein during Ostogenesis by Monoclonal Antibodies," *Molecular and Cellular Biology*8: 2251–2256 (1988).
Kovary and Bravo, "The Jun and Fos Protein Families Are Both Required for Cell Cycle Progression in Fibroblasts," *Molecular and Cellular Biology*11: 4466–4472 (1991).
Kruijer et al., "Induction of the proto–oncogene *fos* by nerve growth factor," *Proc. Natl. Acad. Sci. USA*82: 7330–7334 (1985).
Kruijer et al., "Platelet–derived growth factor induces rapid but transient expression of the c–*fos* gene and protein, "*Nature*312: 711–716 (1984).
Sassone–Corsi et al., "Regulation of Proto–oncogene *fos:* A Paradigm for Early Response Genes," *Cold Spring Harbor Symposia on Quantitative Biology* LIII:749–760 (1988).
Stumpo et al., Insulin and growth factor effects on c–fos expression in normal and protein kinase C–deficient 3T3–LI fibroblasts and adipocytes. Proc. Natl. Acad. Sci. 83: 9453–9457, 1986.*

* cited by examiner

*Primary Examiner*—Scott D. Priebe
(74) *Attorney, Agent, or Firm*—Stephen E. Reiter; Foley & Lardner

(57) ABSTRACT

In accordance with the present invention, there is provided a novel analytical method for identifying compounds which induce and/or inhibit signal transduction in cells. The invention method enables rapid testing of a variety of compounds to determine if they exert an influence on signal transduction. The invention assay can be carried out using unmodified cells and/or cell lines, avoiding the need for extensive preparation prior to analysis.

13 Claims, 1 Drawing Sheet

FUNCTIONAL ASSAYS FOR THE IDENTIFICATION OF LIGANDS WHICH MODULATE SIGNAL TRANSDUCTION

This application is a continuation of application U.S. Ser. No. 08/001,115, filed Jan. 5, 1993, now abandoned, the entire contents of which are hereby incorporated by reference.

ACKNOWLEDGEMENT

This invention was made with Government support under Grant No. CA 44360 awarded by the National Institutes of Health. The Government has certain rights in the invention.

FIELD OF THE INVENTION

The present invention relates to analytical methods. In a particular aspect, the present invention relates to methods for the identification of compounds which induce and/or inhibit signal transduction in cells.

BACKGROUND OF THE INVENTION

Messages are transmitted in cells (and between cells) by a process called signal transduction. Signal transduction is the means by which the presence (or occurrence) of stimuli are communicated within (or between) cells. Since communication within (and between) cells is central to the control of many biological responses, and because many stimuli promote signal transduction, the ability to rapidly monitor signal transduction in response to a given stimulus would be very useful. Such ability would be especially useful for the screening of compounds to identify those capable of modulating signal transduction.

While any viable cell can be used for such screening, especially useful are neuronal cells, which allow the study of signal transduction in the central nervous system. Long-term cell cultures can be obtained from numerous sources, e.g, immortalized cells. The application of the invention techniques, therefore, to a variety of readily available cell types, will allow fundamental questions of cellular and molecular interactions among the myriad of functionally distinct cell types which contribute to development and functioning of mammalian species to be addressed.

BRIEF DESCRIPTION OF THE INVENTION

In accordance with the present invention, we have developed a novel analytical method for identifying compounds which induce and/or inhibit signal transduction in cells. The invention method enables rapid testing of a variety of compounds to determine if they exert an influence on signal transduction. The invention assay can be carried out using unmodified cells and/or cell lines, avoiding the need for cell transformation with labor intensive constructs (e.g., reporter constructs) prior to analysis.

DETAILED DESCRIPTION OF THE INVENTION

Figure 1:
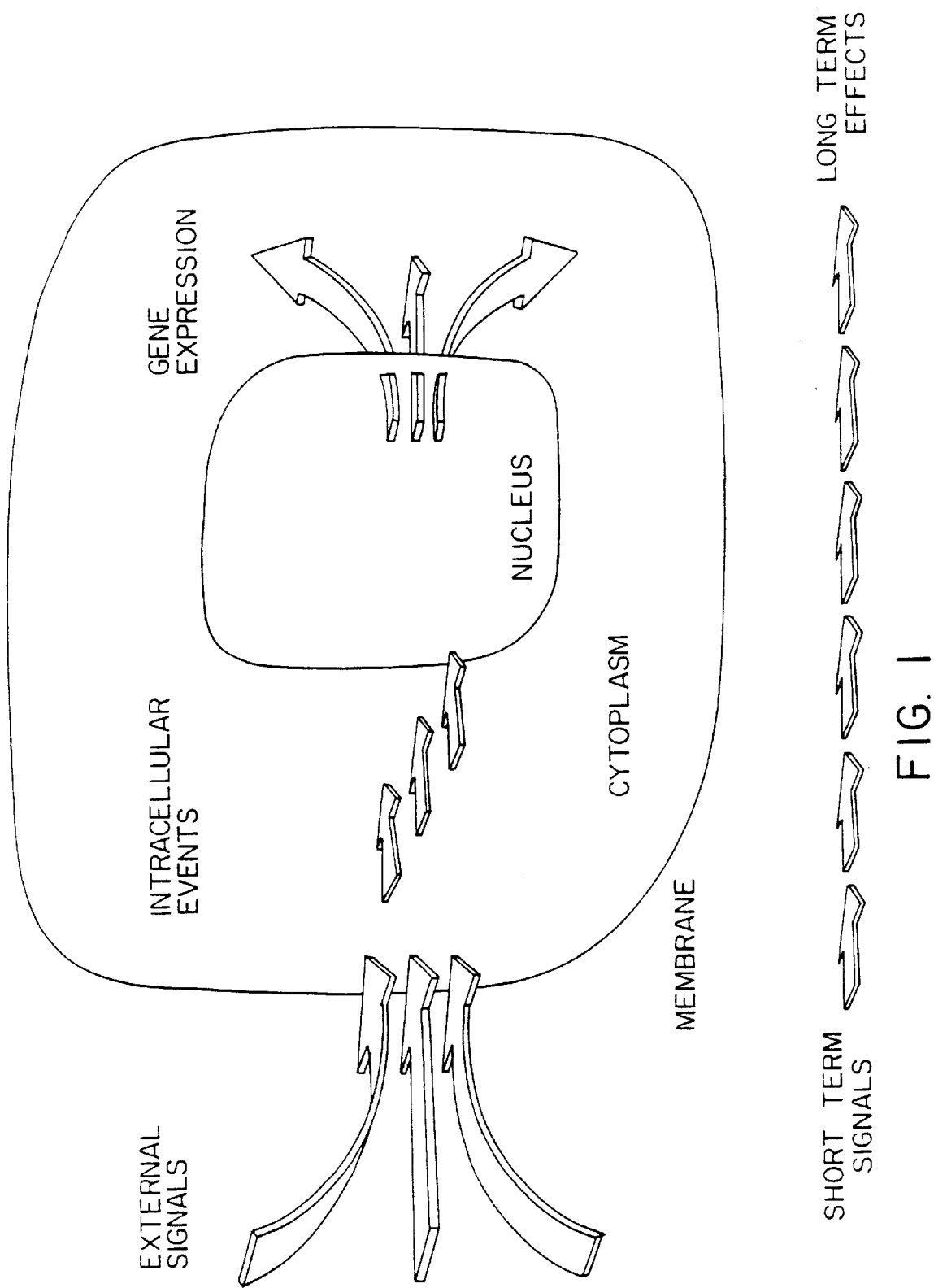
FIG. 1 is a cartoon drawing of the mechanism by which external signals are believed to lead to expression of early response genes.

In accordance with the present invention, there is provided a method for the identification of compounds which are capable of modulating signal transduction in cells, said method comprising:

monitoring expression of early response genes by said cells in response to exposure to said compound, relative to the level of expression of early response genes by said cells in the absence of said compound.

As employed herein, the phrase "early response genes" refers to a family of transcription factors which influence the activity of other genes. The means by which these genes are presently believed to exert their influence is illustrated in the Figure. For example, external signals interact with the cell surface and trigger a cascade of events, resulting in expression of early response genes. Similarly, intracellular events involved in signal transmission operate, through a cascade of events, to induce expression of early response genes. Examples of early response genes include the Fos family of genes, the Myc family of genes, the Jun family of genes, the Myb family of genes, the Rel family of genes, and the like.

As employed herein, the phrase "modulating signal transduction" refers to compounds and/or conditions which either induce or inhibit signal transmission in cells. For example, signal transduction can be induced by a variety of stimuli, such as, for example, heat shock, exposure to neurotransmitters (e.g., excitatory amino acids, inhibitory amino acids), exposuro to growth factors (e.g., nerve growth factor, fibroblast growth factor, epidermal growth factor, epithelial growth factor, and the like), exposure to neuroactive drugs (e.g., lithium, PROZAC® brand antidepressant, a registered trademark of Eli Lilly & Company; etc), exposure to pharmacological agents such as neurotransmitter receptor agonists (e.g., N-methyl D-aspartate, kainate, quinolinate, and the like), neurotransmitter receptor antagonists (e.g., verapamil, lidocaine, and the like), and so on. Similarly, signal transduction can be inhibited by exposure to compounds and/or conditions which interfere with the action of such inducing agents.

Monitoring expression of early response genes as contemplated by the present invention can be carried out in a variety of ways, such as, for example, by monitoring RNA production or protein expression by an early response gene. For example, Northern analysis, RNase protection, antibody-based assays (e.g., ELISA (e.g., sandwich assay), immunoblot, immunofluorescence, immunoprecipitation, etc), and the like can be employed.

Antibodies useful for such monitoring include peptide-based antibodies raised against a member of the Fos, Myc, Jun, Myb, or Rel families of early response proteins, polyclonal antibodies raised against a member of the Fos, Myb, Jun, Myb, or Rel families of early response proteins, or monoclonal antibodies raised against a member of the Fos, Myc, Jun, Myb, or Rel families of early response proteins.

Exemplary antibodies contemplated for use in the practice of the present invention include M2 Fos antibodies (which recognize all members of the Fos family; see, for example, Curran et al., in Mol. Cell,. Biol. 5:167–172 (1985)), anti-c-Fos antibodies, anti-Jun antibodies, anti-c-Jun antibodies, anti-JunB antibodies, anti-JunD antibodies (as described by Kovary and Bravo in Mol. Cell. Biol. 11:2451–2459 (1991)), and the like.

Cell lines contemplated for use in the practice of the present invention include cell lines derived from a variety of sources, such as neuronal cells, muscle cells, epithelial cells, non-neuronal host cells containing genes encoding neuronal receptors, and the like. The cell lines used can be primary cell cultures, immortalized cell lines (e.g., cells transfected with certain oncogenes which confer upon the cells the ability to divide and grow indefinitely), and the like.

Presently preferred host cells for use in the practice of the invention bioassay system are neuronal cells, since cellular and molecular interactions among a myriad of functionally distinct neuronal cell types contribute to the development and functioning of the mammalian central nervous system.

Compounds contemplated for testing in accordance with the invention include those which potentially act as agonists (or antagonists) of cell surface receptors (e.g., glutamate receptors, nicotinic acetylcholine receptors, and the like), intracellular receptors, and the like. Examples of such compounds include pharmacologic agents designed to act at glutamate receptors (e.g., derivatives and/or analogs of N-methyl D-aspartate, kainate, and the like), and so on. In addition, compounds which act as antagonists of such receptors (e.g., derivatives and/or analogs of MK801(i.e., 5-methyl-10,11-dihydro-5H-dibenzo-(a,d)-cyclohepane-5, 10-iminemaleate; dizocilpine, APV (i.e., 2-amino-5-phosphonvaleric acid) and the like) can also be readily tested employing the invention assay method.

In accordance with another embodiment of the present invention, there is provided a method for the identification of compounds which are capable of promoting signal transduction in cells, said method comprising:

monitoring expression of early response genes by said cells in response to exposure to said compound, relative to the level of expression of early response genes by said cells in the absence of said compound.

In accordance with this embodiment of the present invention, compounds which are capable of promoting signal transduction in cells, i.e., agonists, are identified.

In accordance with yet another embodiment of the present invention, there is provided a method for the identification of compounds which are functional as antagonists of ligands which promote signal transduction in cells, said method comprising:

monitoring expression of early response genes in response to exposure to said compound in the presence of one or more ligands which promote signal transduction between said cells, relative to the level of expression of early response genes by said cells in the presence of said ligand(s), but in the absence of said compound.

In accordance with this embodiment of the present invention, compounds which are capable of blocking signal transduction in cells in the presence of agonists, i.e., antagonists, are identified.

In accordance with still another embodiment of the present invention, there is provided a method for the identification of the presence of a specific cell surface receptor on a cell line, said method comprising:

monitoring said cell line for the expression of early response genes when said cell line is exposed to a compound and/or conditions which are known inducers of signal transduction in cells.

The invention comprises a novel method for determining the ability of test compounds to modulate signal transduction in cells. The invention bioassay system utilizes endogenous "signalling" systems present in cells, and therefore does not require the introduction of any recombinant constructs into the test cells. In contrast, prior art assay systems of this sort require introducing one or more plasmids into the test cell, e.g., an "expression"plasmid and/or a "reporter-"plasmid. Alternatively, prior art methodology requires the use of the more involved technique of electrophysiology to establish the functionality of test compounds.

According to the present invention, the expression of any "early response gene" produces a detectable signal. An additional advantage of the present invention is the fact that no separate reporter plasmid is required.

In practicing one aspect of the invention bioassay, the "expression" construct (i.e., DNA encoding a receptor responsive to the test compound) and the "reporter"construct are both natively present in suitable host cells. Host cells are appropriately selected for the presence of cell surface receptors of interest, then cultured in the presence and absence of test compound, which is able to activate (or inhibit) the signal transduction pathway of the cell. The cultured host cells are then monitored for induction (i.e., the presence) or inhibition (i.e., the absence) of expression of the reporter gene sequence (i.e., an early response gene). Finally, according to the invention, the expression product of an early response gene is measured.

The invention bioassay system is especially useful for determining whether a test compound has the ability to induce and/or inhibit signal transduction in a given host cell. The invention bioassay system is also useful for determining whether a test cell has a receptor which is responsive to known agonists and/or antagonists of signal transduction pathways.

The invention bioassay system for testing receptor functionality is a substantial improvement over prior art assays which require the use of two plasmids: an "expression" plasmid and a "reporter" plasmid. According to the present invention, the role played by the expression plasmid and the reporter plasmid are both provided by endogenous sequences of the host cell.

The invention bioassay system allows one to monitor the activation of receptors (endogenously produced by the host cells) by specific compounds, as well as the ability of such compounds to block activation of cell surface receptors.

The invention bioassay overcomes some of the major difficulties encountered in studying the actions of cell surface receptors and ligands therefor. These difficulties include low cellular levels of receptor, possible heterogeneity of receptors, and lack of a quantifiable bioassay system to be a receptor functions. In contrast, existing bioassays are either less sensitive (e.g., transfection-type assays requiring the introduction of a reporter plasmid) than the invention bioassay system, or are substantially more cumbersome (e.g., electro-physiological analyses) than the invention bioassay system.

The invention will now be described in greater detail by reference to the following non-limiting examples.

EXAMPLE 1

Induction of the Early Response Gene, Fos, by Nerve Growth Factor, $K^+$ Depolarization, Epidermal Growth Factor and Phorbol Ester PC12 cells were grown in Dulbecco's modified Eagle's medium containing 10% fetal calf serum and 5% horse serum as described by Schubert et al. in Brain Res. Vol. 190:67–69 (1980)]. For induction, the culture medium was aspirated and replaced by N2 medium [see Bottenstein and Sato, Proc. Natl. Acad. Sci. USA Vol. 76:514–517 (1979)]. Exponentially dividing cultures were used at a density of $5 \times 10^6$ cells per 100 mm culture dish. β-NGF was used at 50 ng/ml.

Total cellular RNA wag isolated by the method of Chirgwin et al. [see Biochemistry Vol. 18:5294–5299 (1977)], and was analyzed by electrophoresis through 0.8% agarose/formaldehyde gels [Lehrack et al., Biochemistry Vol. 16:4743–4748 (1977)], followed by RNA blot transfer to nitrocellulose [Thomas, P. S., Proc. Natl. Acad. Sci. USA Vol. 77:5201–5205 (1980)] and hybridization to radioactive fos probe as previously described [see, for example, Curran et al., J. Virol. Vol. 44:674–682 (1982); Mitchell et al., Cell Vol. 40;209–217 (1985); and Rigby et al., J. Mol. Biol. Vol. 113:237–257 (1977)].

For immunoprecipitation, PC12 cells were labeled for 20 minutes in 5 ml of N2 medium with reduced methionine with [$^{35}$S]methionine at 0.1 mCi/ml (New England Nuclear; 600–1000 Ci/mmol; 1 Ci=17 GBq). The cultures were washed with ice-cold Tris-buffered saline and lysed with 1.0 ml of RIPA buffer (0.15 M NaCl/1% Nonidet P-40/1% sodium deoxycholate/0.1% NaDodSO$_4$/2 mM EDTA/100 units of TRASYLOL® brand chemotherapeutic, a registered trademark of Bayer Aktiengesellschaft per ml/10 mM sodium phosphate, pH 7.0). Lysates were clarified at 20,000×g for 60 minutes at 4° C. and incubated with either M2 peptide antiserum [see Curran At al., Mol. Cell Biol. Vol. 5:167–172 (1985)] or normal rabbit serum. The M2 antiserum is directed against a synthetic peptide of residues 127–152 of the fos protein. After 1 hour at 0° C., 25 μg of PANSORBIN® brand *staphylococcus aureus* cells, a registered trademark of Calbiochem-Behring Corporation (Calbiochem) was added for 30 minutes. Immunoprecipitates were centrifuged through a solution of 10% (wt/vol) sucrose in RIPA buffer and then washed repeatedly by centrifugation in RIPA buffer [Beemon and Hunter, J. Virol. Vol. 28:551–566 (1978)]. Precipitates were analyzed on 8% polyacrylamide gels [see Laemmli, U. K., Nature (London) Vol. 227:6010–6025 (1970); Bonner and Laskey, Eur. J. Biochem. Vol. 46:83–88 (1974); and Cochran et al., Science Vol. 226:1080–1082 (1984)].

Addition of NGF to proliferating subconfluent cultures of rat PC12 cells results in a rapid induction of fos mRNA. A 2.2 kilobase fos mRNA is detectable within 5 minutes after NGF addition, is maximally abundant after 30 minutes, and decreases thereafter. No specific fos transcription can be detected by RNA blot analysis of RNA from uninduced PC12 cells, but sensitive RNA protection techniques reveal very low levels of fos mRNA [Kruijer et al., Nature (London) Vol. 312:711–716 (1984)].

fos proteins are also synthesized in PC12 cells in response to NGF. PC12 cells were exposed to NGF for 30, 60, and 240 minutes, followed by labeling of the cultures with [$^{35}$S]methionine for 20 minutes. fos protein synthesis was detected 30 and 60 minutes after NGF addition. The labeled protein was very heterogeneous with apparent molecular masses between 55 and 65 kDa. Little or no fos protein synthesis could be detected 240 minutes after induction. Two proteins of 39 and 37 kDa were coprecipitated with fos protein by immune serum but not by nonimmune serum. It has previously been shown that boiling of cell lysates in 0.5% sodium dodecyl sulfate prior to precipitation with M2 antiserum prevented precipitation of p39 and p37, suggesting that these proteins are complexed with fos proteins [Curran et al. (1985) supra]. Low amounts of the p39/37 were precipitated 16 hours after NGF addition, indicating that small amounts of fos proteins were present at later times. It is possible that late after induction, the fos proteins are too heterogeneous, due to postsynthetic modification, to be detected by gel electrophoresis [curran et al., Cell Vol. 36:259–268 (1984)].

Early response genes, such as genes encoding fos proteins, have previously been localized in the nucleus [Curran et al. (1984) supra]. To establish that NGF-induced fos proteins are also nuclear, cells were fractionated into nuclear and cytoplasmic compartments 30 minutes after exposure to NGF. Induced fos proteins are primarily located in the pellet (nuclear) fraction. No fos protein could be detected if the antiserum was first incubated with M2 peptide.

Binding of NGF to its cell-surface receptors causes a rapid (within minutes) and transient increase in intracellular cAMP levels [see Schubert et al., Nature (London) Vol. 273:718–723 (1978); and Traynor and Schubert, Dev. Brain Res. Vol. 14:197–203 (1984). Increasing intracellular cAMP in PC12 cells by means other than NGF causes neurite outgrowth, enzyme inductions, and protein synthesis and phosphorylations that are qualitatively identical to those observed with NGF, indicating that cAMP may act as a second messenger in the NGF response [Schubert, D., Developmental Biology of Cultured Nerve, Muscle, and Glia (Wiley, N.Y.), pp. 122–155 (1984)]. The effect of cAMP (and its functional derivative, dibutyryl cAMP (Bt$_2$cAMP)) on fos mRNA and protein expression was, therefore, analyzed. Addition of Bt$_2$cAMP to proliferating PC12 cells induces the fos gene, although with slightly slower kinetics than NGF. The fos mRNA is maximally abundant after 60 minutes as compared to 30 minutes in cells induced with NGF. No fos-specific RNA is detected at 240 minutes, but small amounts of fos mRMA can be detected by RNA blotting, 20 hours after the cells are exposed to Bt$_2$cAMP.

fos proteins could be immunoprecipitated from cells 15–60 minutes after the addition of Bt$_2$cAMP. By 240 minutes, only small amounts of fos protein were detected, but no fos proteins were immunoprecipitated 20 hours after addition of Bt$_2$cAMP (when fog mRNA levels are clearly increased). Since Bt$_2$cAMP can have some nonspecific effects on cells [see, for example, Prasad and Sinha, In Vitro Vol. 12:125–132 (1976)], the effect of cAMP itself on the expression of fos proteins was also investigated. cAMP induced the synthesis of fos proteins with identical kinetics but with lower efficiency than Bt$_2$cAMP. These results indicate that a transient increase in cAMP levels can mimic the effect of NGF in activating the fog gene.

Exogenous K$^+$ induces neurite outgrowth without a detectable increase in the level of intracellular cAMP [Traynor and Schubert (1984) supra]. It causes an influx of Ca$^{2+}$ ions, which can directly stimulate neurite extension in PC12 cells [see Schubert et al. (1978) supra; Traynor and Schubert (1984) supra; and Schubert. D. (1984) supra]. K$^+$ (50 mm) induced fos RNA with similar kinetics as Bt$_2$-cAMP. Since K$^+$ depolarization does not lead to an increase in cAMP, these data show that fos activation can occur in the absence of an increase in intracellular cAMP.

PC12 cells contain distinct cell-surface receptors for EGF and NGF [Huff and Guroff, J. Cell. Biol. Vol. 88:189–198 (1984)]. Although EGF does not cause neuronal differentiation, it does have some effects on responsive cells that are similar to those induced by NGF. Both NGF and EGF stimulate sodium influx and an initial increase in the rate of proliferation [Boonstra et al., J. Cell Biol. Vol. 97:92–98 (1983)]. The phorbol ester phorbol 12-myristate 13-acetate (PMA) is similar to EGF in that it induces cell proliferation [see Dicker and Rosenquist, Nature (London) Vol. 287:607–612 (1980)]. EGF and PMA both induce fos RNA and fos proteins with overall kinetics similar to those of NGF. In contrast to EGF and PMA, insulin does not increase fos protein or mRNA.

The above data show that fos mRNA and protein are rapidly induced in response to compounds such as NGF, cAMP, EGF, PMA and K$^+$ depolarization, while insulin is ineffective for inducing fos expression in PC12 cells.

EXAMPLE 2

Induction of the Early Response Gene, Fos, in Fibroblasts by Platelet-derived Growth Factor, Fibroblast Growth Factor or the Phorbol Ester, TPA 150 mm dish cultures of NIH 3T3 cells were grown in Dulbeccol's modified Eagle's medium (DMEM) Containing 10% calf serum (CS). After reaching confluence the medium was replaced with 20 ml of DMEM 0.5% CS for 1 day. Partially purified PDGF (0.4% from CM-Sephadex, see Raines and Ross, J. Biol. Chem. Vol. 257:5154–5160 (1982)—at this step of the purification, PDGF concentration assayed by mitogenesis equals the concentration estimated by radioreceptor assay [see Bowen-Pope and Ross, J. Biol. Chem. Vol. 257:5161–5171 (1982)]) was dissolved in 1 mM acetic acid and added to a final concentration of 0.83 nM. The same volume of a solution of bovine serum albumin (BSA, 1 mg/ml) dissolved in 1 mM acetic acid was added to a control dish. Cycloheximide (35 $\mu$M) was added 2 minutes before PDGF. Tetradecanoylphorbol-13-acetate (TPA; 250 $\mu$g/ml) was added from a stock solution in dimethyl sulphoxide (DMSO): the final DMSO concentration was 0.25%. After induction the cells were lysed in 4 M guanidine thiocyanate and total RNA was isolated as described by Chirgwin et al. in Biochemistry Vol. 18:5294–5299 (1977). RNA was quantitated by measuring $A_{260}$. A 1,137-bp SmaI-SmaI fragment, spanning the 5'-untranscribed region and the first exon and part of the first intron of the mouse c-fos gene, was cloned in the SmaI site of the expression vector pRVII7Z2 (provided by Dr. Angerer).

To generate run-off transcripts, the plasmid was linearized by HindIII, which cuts just downstream of the inserted c-fos sequence relative to the site of to SP6 phage promoter in pRVIIΔ7Z2. cRNA run-off transcripts were synthesized in a reaction mixture containing 40 mM Tris-HCl pH 7.5, 6 mM $MgCl_2$, 10 mM dithiothreitol (DTT), 50 U/ml RNasin (Promega Biotec), 400 $\mu$M GTP, ATP and CTP, 13 $\mu$M $\alpha^{32}$P-UTP (650 Ci/mmol; ICN), 1 $\mu$g linearized template and 1,000 U/ml SP6 phage polymerase (isolated according to Butler and Chamberlain, J. Biol. Chem. Vol. 257:5772–5778 (1982)) for 1 hour at 40° C.

Total RNA (10 $\mu$g) was mixed with 5 ng $^{32}$P-labelled cRNA (specific activity 109 d.p.m./$\mu$g) in 30 $\mu$l 0.4M NaCl, 1 mM EDTA, 80% formamide, 40 mM PIPES, pH 6.5. The mixture was heated at 85° C. for 5 minutes and incubated for 4 hours at 37° C, then for 10 hours at 30° C. After hybridization, 300 $\mu$l of RNase digestion buffer (5 mM EDTA, 300 mM NaCl, 10 mM Tris-HCl, pH 7.5) were added containing 30 $\mu$g/ml RNase A and 2 $\mu$g/ml RNase T1 and incubated for 30 minutes at 30° C. RNase digestion was stopped by adding SDS (final concentration 0.7%) and proteinase K (0.15 $\mu$g/ml) and incubation Was continued for 30 minutes at 37° C. The samples were extracted once with phenol/chloroform and ethanol-precipitated with 10 $\mu$g tRNA as carrier and 1.0 M ammonium acetate. The precipitates were dissolved and reprecipitated with 0.5 M ammonium acetate. Dried pellets were resuspended in 5 $\mu$l formamide/dye mixture and loaded on a 5% sequencing gel containing 8.3 M urea and 90 mM Tris-borate pH 8.3: 2.5 mM EDTA. The gel was exposed with a fluorescent screen for 3.5 hours at −70° C.

Confluent cultures of NIH 3T3 cells were exposed to 0.83 nM PDGF for 4 hours in the continuous presence of 35 $\mu$M cycloheximide, which inhibited protein synthesis by >95%. PDGF alone increased the content of c-fos RNA threefold, the combination of PDGF and cycloheximide increased the level two-fold. Puromycin also augmented the increase in c-fos RNA. This suggested that protein synthesis was unnecessary for, and might even inhibit, an increase in c-fos RNA content, for example, by attenuation of transcription and/or by stimulating c-fos RNA degradation.

Next, it was tested whether brief exposure of resting fibroblast cultures to PDGF would induce c-fos RNA. The c-fos gene transcripts were characterized by hybridization with $^{32}$P-labelled complementary RNA (cRNA) synthesized using SP6 phage polymerase [see Green et al. in Cell Vol. 32:681–694 (1983)], followed by ribonuclease digestion and electrophoresis of the protected cRNA. The cRNA probe was transcribed from a SmaI fragment of 1,137 nucleotides encompassing the putative murine c-fos gene promoter, the first exon and part of the first intron [Van Beveren et al., Cell Vol. 32:1241–1255 (1983)]. If transcription starts at the presumed 5'-cap site then the primary, unspliced transcripts should protect 637 nucleotides of the probe and the spliced mature mRNA should protect 289 nucleotides of the cRNA from ribonuclease digestion. Ribonuclease-resistant hybrids of ~289 nucleotides were formed with RNA extracted from PDGF-treated NIH 3T3 cell cultures; this band was undetectable with RNA from untreated cultures. Quantification of this band indicated at least 20-fold induction of c-fos mRNA by 20 minute exposure of calls to PDGF. Addition of PDGF plus cycloheximide for 60 minutes resulted in a 50-fold increase in spliced c-fos RNA relative to a ninefold increase with PDGF alone. By measuring the radioactivity in the 289-nucleotide fragment, it can be estimated that after a 20 minute exposure to PDGF, 0.0001% of NIH 3T3 cell RNA (0.005% mRNA) is c-fos mRNA. Assuming a cellular RNA content of 6 pg, this corresponds to about 5–10 copies of c-fos mRNA per cell after 20 minutes of induction. Essentially identical kinetics of induction were observed with RNA from stimulated cultures of BALB/c/3T3 cells.

Next, protein products of the c-fos gene were assayed by immunoprecipitation of $^{35}$S-methionine-labelled cultures using an antiserum directed against a 26-amino acid peptide (M2 peptide, residues 127–152 of the 380-amino acid predicted c-fos protein, see Van Beveren et al., (1983) supra; and Curran et al., Molec. Cell Biol. 5:167–172 (1985)). BALB/c/3T3 cell cultures were labelled with $^{35}$S-methionine for 30 minutes, starting at various times after addition of 0.67 nN PDGF. BALB/c/3T3 cell cultures were treated with 0.67 nM pure PDGF for 0, 30, 90 or 150 minutes before the addition of 100 $\mu$Ci of $^{35}$S-methionine. Another culture received an equivalent volume of BSA in 1 mM acetic acid for 30 minutes before labelling. After a further 30 minutes of incubation, cultures were washed, lysed and one-third volumes were immunoprecipitated with 1 $\mu$q IgG equivalent of non-immune rabbit serum or 1 $\mu$g affinity-purified IgG to M2 peptide. Immunoprecipitates were analyzed by SDS-polyacrylamide gel electrophoresis.

Six to eight polypeptides were immunoprecipitable from PDGF-treated cultures, but not from control cultures. Some of these proteins are c-fos gene products and some are unrelated. Exposure to PDGF for as little as 30 minutes induced labelling of these immunoprecipitated proteins with hardly any change in the overal rate of protein synthesis. Labelling was maximal by 60 minutes after addition of PDGF, and was decreased markedly 3 hours after PDGF addition. The relative incorporation of $^{35}$S-methionine into each protein varied with time; the apparent sizes of all the species of relative molecular mass ($M_r$) between 56,000 (56K) and 72K seemed to increase slightly 30–60 minutes after PDGF addition. None of these proteins was immunoprecipitated using non-immune rabbit serum, nor if excess M2 peptide was used to block specific binding to M2-peptide antiserum.

To elucidate the identities of the immunoprecipitated proteins, NIH 3T3 cells were labelled with $^{35}$S-methionine for 30 minutes, starting 30 minutes after addition of 0.83 nM PDGF; lysates were immunoprecipitated with antiserum to M peptide or with TBRS (i.e., sera from rats with v-fos-induced tumors). Portions of a NIH 3T3 cell lysate (labelled for 30 minutes starting 30 minutes after addition of 0.83 nM pure PDGF) and a R-MMV cell lysate (labelled for 30 minutes) representing ¹/₂₀ of a 35-mm dish culture in each case, were immunoprecipitated with 1 μl normal rat serum, 1 μl TBRS, 1 μl TBRS mixed with 1 μg M2 peptide or 0.3 μg affinity-purified IgG to M2 peptide. For labelling conditions see below. Except where noted, confluent 35-mm dish cultures of 3T3 cells were incubated in 1 ml DMEM containing 1% normal methionine concentration and 0.5% CS for 40–48 hours. Additions of PDGF (essentially homogeneous, purified through phenyl-Sepharose [see Raines and Ross, (1982) supra], dissolved in 1 mM acetic acid containing 1 mg/ml BSA), or an equal volume of 1 mg/ml BSA in 1 mM acetic acid, and $^{35}$S-methionine (100 μCi of ~1,000 Ci/mmol; Amersham/Searle) were made directly to the medium. Cultures were lysed after washing with cold Tris-buffered saline by adding 0.5 ml of RIPA buffer (0.15 m NaCl, 1% Nonidet P-40, 1% sodium deoxycholate, 0.1% SDS, 1 mM EDTA, 100 U/ml TRASYLOL®, 10 mM sodium phosphate, pH 7.0) and scraping. Lysates were clarified at 20,000 g for 60 minutes at 4° C. IgG or antisera were added as indicated. After 1 hour at 0° C., 1 mg PANSORBIN® (Calbiochem) was added for 1 hour. Immunoprecipitates were centrifuged through a solution of 10% sucrose in RIPA, then washed repeatedly by centrifugation in RIPA [see Sefton et al. in J. Virol. Vol. 38:957–971 (1978)]. Immunoprecipitations with rat antitumor serum or normal rat serum utilized goat antiserum to rat IgG added 30 minutes before Pansorbin. Immunoprecipitates were dissociated by incubation at 100° C. for 2 minutes in 2% SDS, 20% 2-mercaptoethanol, 10% glycerol, 0.1 M Tris-HCl, pH 6.8, and one-half of each sample analyzed on a SDS-polyacrylamide gel (12.5% acrylamide/0. 10% bis-acrylamide—see Laemmli, U. K., Nature Vol. 227:680–685 (1970)). Gels were stained to visualize marker β-galactosidase, phosphorylase, BSA, ovalbumin and carbonic anhydrase and impregnated with diphenyloxazole (PPO) [Bonner and Laskey, Eur. J. Biochem. Vol. 46:83–88 (1974)]. Dried gels were exposed to pre-sensitized film at −70° C. Exposure times: a, 10 days; b, 4 days.

TBRS specifically precipitated the 56–72K proteins recognized by M2-peptide antiserum but was less efficient at precipitating the presumed p39 proteins and failed to precipitate two proteins of $M_r$ 45K and 46K (p45 and p46). These two proteins were not precipitated in appreciable amounts from R-MMV cells with either TBRS or M2-peptide antiserum. Tryptic peptide analysis confirmed that all four immunoprecipitated proteins of $M_r$ 56–72K were homologous to each other and to two authentic murine c-fos gene products synthesized in R-MMV cells. Thus the different sizes of the c-fos products in NIH 3T3 cells and R-MMV cells presumably result from differential post-translational modification. The $M_r$ 39K proteins precipitated from PDGF-stimulated NIH 3T3 mouse cells and from R-MMV rat cells were also highly conserved. p45 and p46 were very similar and also shared some peptides with p39.

Protein labelling was carried out by incubating a confluent 35-mm dish culture of NIH 3T3 cells for 2 days in DMEM containing 1% normal methionine concentration and 0.5 CS. The volume wag then reduced to 0.4 ml and 0.83 nM pure PDGF was added for 30 minutes followed by 2 mCi $^{35}$S-methionine for 30 minutes. A 35-mm culture of R-MMV cells (clone MMV6B) was incubated for 30 hours in DMEM containing 1% normal methionine concentration and 5% dialysed CS before the volume was reduced to 0.4 ml and 1 mCi $^{35}$S-methionine added for 30 minutes. Cultures were washed, lysed and four-fifths of each sample immunoprecipitated with 3 μg affinity-purified IgG to M2 peptide. Polypeptides were excised from the dried gel, eluted, oxidized with performic acid and digested with trypsin as described by Beemon and Hunter in Virology 28:551–566 (1974). Half of each digest was analyzed by electrophoresis at pH 4.72 and ascending TLC [Gibson, W., Virology Vol. 62;319–336 (1974)]. Chromatograms were dipped in molten 2-methylnaphthalene containing 0.4% PPO and exposed to pre-sensitized film at −70° C.

The dependence of p56–72 $^{c\text{-}fos}$ induction on PDGF concentration was then investigated by labelling with $^{35}$S-methionine for 30 minutes, starting 30 minutes after PDGF addition. Thus, BALB/c/3T3 cells were exposed to various concentrations of pure PDGF, diluted in 1 mM acetic acid containing 1 mg/ml BSA, for 30 minutes before the addition of $^{35}$S-methionine for 10 minutes. The final concentrations of PDGF were 0, 0.074 nM, 0.22 nM, 0.67 nM, or 2.0 nM. Each lysate was immunoprecipitated with nonimmune immune rabbit serum, 1 μg affinity-purified IgG to M2 peptide, or 1 μg IgG to M2 peptide preincubated with 3 μg M2 peptide. All the samples were run on the same gel and exposed for 10 days. Similarly, NIH 3T3 cells were exposed to BSA, pure PDGF (2.5 nM), TPA (0.1 mg/ml), EGF (8.3 nM) or FGF (0.12 μg/ml; see Gospodarowicz et al. in J. Biol. Chem. Vol. 253:3736–3743 (1978) for 30 minutes before the addition of $^{35}$S-methionine for 30 minutes. Each sample was immunoprecipitated with non-immune rabbit serum or affinity-purified IgG to M2 peptide. All samples were run on the same gel and exposed for 5 days.

With either NIH 3T3 cells or BALB/c/3T3 cells c-fos protein synthesis was maximal at PDGF concentrations that saturate PDGF binding sites at 37° C. (1.0 nM—see, for example Heldin et al. in Proc. Natl. Acad. sci. USA Vol. 78:3664–3668 (1981); Bowen-Pope and Ross, (1982) supra; and Cooper et al. in Cell Vol. 31:263–273 (1982)) and half-maximal at the concentration for half-maximal binding (0.3–0.5 nM—see, for example, Bowen-Pope and Ross, (1982) supra; and Cooper et al., (1982) supra). These doses are greater than those required for stimulation of DNA synthesis (half-maximal below 0.1 nM—see Antoniades et al., Proc. Natl. Acad. Sci. USA Vol. 76:1809–1813 (1979); Heldin et al., Proc. Natl. Acad. Sci. USA Vol. 76:3722–3726 (1979); and Raines and Ross, (1982) supra) p56–72$^{c\text{-}fos}$ synthesis was detectable at 50% mitogenic doses of PDGF, however. The rate of p56–72$^{c\text{-}fos}$ synthesis was difficult to quantify because of the number of species involved, but may approach 0.005% of total protein synthesis during the 30-minute labelling period. Synthesis of p56–72$^{c\text{-}fos}$ was also stimulated by basic pituitary FGF (120 ng/ml) or TPA (100 μg/ml), but was increased only slightly by EGF (8.3 nM).

While the invention has been described in detail with reference to certain preferred embodiments thereof, it will be understood that modifications and variations are within the spirit and scope of that which is described and claimed.

That which is claimed is:

1. A method for identifying compounds which modulate signal transduction in cells, said method comprising:

exposing cells to a compound, wherein said cells contain nucleic acids encoding at least one endogenous early response gene and express said gene in the absence of said compound, and wherein the ability of said compound to modulate signal transduction in said cells is unknown; and thereafter monitoring said cells for changes in early response gene expression levels wherein such changes indicate a compound which modulates signal transduction in said cells, wherein said early response gene is selected from the Myc, Jun, Myb, or Rel families of genes.

2. A method according to claim 1 wherein said compound is an agonist.

3. A method according to claim 1 wherein said compound is an antagonist.

4. A method according to claim 1 wherein said cells have cell receptors and said compound modulates signal transduction via said cell receptors.

5. A method according to claim 1 wherein expression of said early response gene is monitored by antibody-based assays selected from ELISA, immunoblot, immunofluorescence, or immunoprecipitation.

6. A method according to claim 5 wherein the antibody employed for said monitoring is selected from the group consisting of polyclonal antibodies and monoclonal antibodies; wherein said antibodies are raised against a member of the group consisting of Myc, Jun, Myb, and Rel families of early response proteins, or fragments thereof.

7. A bioassay for identifying compounds which promote signal transduction in cells, said bioassay comprising:

exposing cells to a compound, wherein said cells contain nucleic acids encoding at least one endogenous early response gene and express said gene in the absence of said compound, and wherein the ability of said compound to promote signal transduction in said cells is unknown; and thereafter monitoring said cells for changes in early response gene expression levels wherein changes comprising an increased level of expression indicate a compound which promotes signal transduction in said cells, wherein said early response gene is selected from the Myc, Jun, Myb, or Rel families of genes.

8. A bioassay according to claim 7 wherein expression of said early response gene is monitored by ELISA, immunoblot, immunofluorescence, or immunoprecipitation.

9. A bioassay according to claim 7 wherein said cells have cell surface receptors and said compound modulates signal transduction via said receptors.

10. A bioassay for identifying compounds which are antagonists of (i) cell surface receptors, or (ii) conditions which promote signal transduction in cells, or (iii) both tell surface receptors and conditions which promote signal transduction in cells, said bioassay comprising:

exposing suitable cells to a compound under physiological conditions, wherein said cells contain nucleic acids encoding at least one endogenous early response gene and express said gene in the absence of said compound, wherein the ability of said compound to inhibit signal transduction in said cells is unknown; and further exposing said cells to (i) a fixed concentration of at least one ligand, or (ii) a condition known to promote signal transduction in said cells, or (iii) a fixed concentration of at least one ligand and a condition known to promote signal transduction in said cells; and thereafter monitoring said cells for changes in early response gene expression levels wherein changes comprising a decreased level of expression indicate a compound which is an antagonist of (i) said ligand, or (ii) a condition which promotes signal transduction in cells, or (iii) both said ligand and said condition, wherein said early response gene is selected from the Myc, Jun, Myb, or Rel families of genes.

11. A bioassay according to claim 10 wherein signal transduction is induced by stimuli selected from heat shock, neurotransmitters, growth factors, or neuroactive drugs.

12. A bioassay according to claim 10 wherein expression of said early response gene is monitored by ELISA, immunoblot, immunofluorescence, or immunoprecipitation.

13. A method according to claim 10 wherein said cells have cell receptors and said compound modulates signal transduction via said cell receptors.

* * * * *

UNITED STATES PATENT AND TRADEMARK OFFICE
CERTIFICATE OF CORRECTION

PATENT NO.     : 6,326,138 B1
DATED          : December 4, 2001
INVENTOR(S)    : Verma et al.

It is certified that error appears in the above-identified patent and that said Letters Patent is hereby corrected as shown below:

Column 12,
Line 6, change "tell" to -- cell --

Signed and Sealed this

Eighteenth Day of February, 2003

JAMES E. ROGAN
*Director of the United States Patent and Trademark Office*